(12) United States Patent
Jörgensen

(10) Patent No.: US 7,963,460 B2
(45) Date of Patent: Jun. 21, 2011

(54) DETACHABLE AROMATIC NEBULIZING DIFFUSER

(75) Inventor: Carsten Jörgensen, Kastanienbaum (CH)

(73) Assignee: Ming Jen Hsiao, Miaoli County (TW)

( * ) Notice: Subject to any disclaimer, the term of this patent is extended or adjusted under 35 U.S.C. 154(b) by 122 days.

(21) Appl. No.: 12/552,341

(22) Filed: Sep. 2, 2009

(65) Prior Publication Data

US 2011/0051983 A1 Mar. 3, 2011

(51) Int. Cl.
*B05B 1/08* (2006.01)
*B05B 17/04* (2006.01)
*B05B 15/00* (2006.01)

(52) U.S. Cl. .................. 239/102.2; 239/102.1; 239/289; 239/338

(58) Field of Classification Search ........... 239/4, 102.1, 239/102.2, 288, 288.3, 288.5, 289, 302, 337, 239/338, 432; 128/200.14, 200.16, 200.18, 128/200.21; 261/78.1, 78.2, DIG. 48, DIG. 65; 362/96

See application file for complete search history.

(56) References Cited

U.S. PATENT DOCUMENTS

| | | | | |
|---|---|---|---|---|
| 3,901,443 A | * | 8/1975 | Mitsui et al. | 239/102.2 |
| 4,640,804 A | * | 2/1987 | Mizoguchi | 261/81 |
| 4,644,790 A | * | 2/1987 | Mizoguchi | 73/293 |
| 5,881,714 A | * | 3/1999 | Yokoi et al. | 128/200.14 |
| 5,881,715 A | * | 3/1999 | Shibasaki | 128/200.14 |
| 6,543,701 B1 | * | 4/2003 | Ho | 239/102.1 |

* cited by examiner

*Primary Examiner* — Darren W Gorman
(74) *Attorney, Agent, or Firm* — Ming Chow; Sinorica, LLC

(57) ABSTRACT

A detachable aromatic nebulizing diffuser includes a base panel, an electric fan, a fluid container, an ultrasonic oscillator, a power jack, a water baffle, a lower housing and a top cover. The ultrasonic oscillator oscillates ultrasonic waves to cause an aromatic fluid in the fluid container into a fine mist that is carried by currents of air caused by the electric fan and guided through an air duct in the fluid container. The fluid container has bottom mounting rods detachably plugged into respective tubular upright posts of the base panel, facilitating mounting and dismounting. The water baffle and the top cover are light transmissive for creating a visual effects upon working of a light source that is carried on the ultrasonic oscillator.

10 Claims, 7 Drawing Sheets

DETACHABLE AROMATIC NEBULIZING DIFFUSER

BACKGROUND OF THE INVENTION

1. Field of the Invention

The present invention relates to a nebulizing diffuser and more particularly, to a detachable aromatic nebulizing diffuser that diffuses essential oils or any of a variety of aromatic fluids on a refreshing current of air rapidly and efficiently.

2. Description of the Related Art

Regular aromatic nebulizing diffusers or essential oil diffusers commonly use an ultrasonic oscillator to generate a high ultrasonic energy for causing atomization of an essential oil for application. Separation of electric charges in falling rain, caused by breaking up of the water droplets, the drops becoming positively charged and the air negatively charged. This separation of electric charges accompanying the aerodynamic breakup of water drops is known as spray electrification, the waterfall effect or Lenard effect. Conventional aromatic nebulizing diffusers simply produce an upwardly flying mist of aromatic vapor. They cannot simulate the natural visual effect of a flying mist caused by the impact of a waterfall.

Further, conventional essential oil nebulizing diffusers with light emitting means cannot exhibit a lighting effect apparently at daylight. Due to the use of a light-tight housing, conventional essential oil nebulizing diffusers cannot create a colorful mist scenery at night.

Further, conventional aromatic nebulizing diffusers commonly use screws to affix component parts together, complicating mounting and dismounting procedures. After a long use, the inside wall of the aromatic nebulizing diffusers may be covered with a layer of dirt. It takes much time and labor to practice a cleaning work.

Further, the opening of a regular aromatic nebulizing diffuser has a diameter gradually reducing from the inside toward the outside. This gradually reducing diameter design tends to cause the generated fine mist to be condensed into water drops, lowering the fin mist generating performance.

Further, conventional aromatic nebulizing diffusers may use an electric fan to cause currents of air for flashing an essential oil into a mist. However, due to limited air path, the pressure of the induced currents of air is not sufficient for causing a fine mist in a big area, lower the nebulizing diffusing performance.

Further, conventional aromatic nebulizing diffusers commonly have the fine mist output mouse arranged in vertical at the top side, the generated fine mist can simply be lifted by air in vertical. If an aromatic nebulizing diffuser is placed in a corner area of a house, the generated fine mist will not be evenly distributed in the house.

Therefore, it is desirable to provide an aromatic nebulizing diffuser that eliminates the drawbacks of the aforesaid conventional designs.

SUMMARY OF THE INVENTION

The present invention has been accomplished under the circumstances in view. It is main object of the present invention to provide an aromatic nebulizing diffuser, which is easily detachable, facilitating cleaning work.

It is another object of the present invention to provide a detachable aromatic nebulizing diffuser, which utilizes a tapered air duct to work with an electric fan, thereby enhancing the flowing speed of the currents of air caused by the electric fan and the formation of a fine mist.

It is still another object of the present invention to provide a detachable aromatic nebulizing diffuser, which enables a user to see the presence of an uplifting flow of air that carries a fine mist of aromatic fluid molecules toward the outside open air.

It is still another object of the present invention to provide a detachable aromatic nebulizing diffuser, which allows adjustment of the fine mist spraying angle, so that the generated fine mist can be evenly distributed into the expected space area.

To achieve these and other objects of the present invention, a detachable aromatic nebulizing diffuser comprises a base panel, the base panel comprising a plurality of air vents cut through top and bottom walls thereof and a plurality of tubular upright posts perpendicularly upwardly extended from the top wall; an electric fan mounted on the base panel corresponding to the air vents and operable to draw outside fresh air upwardly through the air vents; a fluid container, the fluid container comprising a horizontal bottom wall, a vertical peripheral wall, a fluid chamber surrounded by the horizontal bottom wall and the vertical peripheral wall and holding an aromatic fluid, an air duct suspending in the fluid chamber, the air duct having an air inlet disposed at a bottom side of the horizontal bottom wall and facing the electric fan for guiding in currents of air from the electric fan, an air outlet disposed at a top side thereof, and a diameter gradually reducing in direction from the air inlet toward the air outlet, a plurality of bottom mounting rods perpendicularly downwardly extended from the horizontal bottom wall and respectively detachably plugged into the tubular upright posts of the base panel, and a center mounting hole cut through the horizontal bottom wall at the center; an ultrasonic oscillator mounted in the center mounting hole of the fluid container for generating oscillation energy to cause the aromatic fluid in the fluid chamber into a fine mist; a power jack mounted on the base panel and electrically connected with the electric fan and the ultrasonic oscillator for providing the electric fan and the ultrasonic oscillator with the necessary working voltage; a water baffle, the water baffle comprising a tongue plate and a pipe connector connected to the tongue plate, the pipe connector comprising a connector housing and two retaining rods suspending in the connector housing and plugged into the air outlet of the air duct to hold the tongue plate above the ultrasonic oscillator and the aromatic fluid contained in the fluid chamber, the two retaining rods and the connector housing defining at least one air jet for ejection of a flow of air from the air outlet of the air duct toward the aromatic fluid in the fluid chamber; a lower housing surrounding the base panel, power jack, the electric fan, the fluid container and the ultrasonic oscillator; and a top cover covering the fluid container and the lower housing, the top cover comprising a bottom opening disposed at a bottom side thereof and coupled to the fluid container and a top muzzle disposed at a top side thereof in communication with the bottom opening and the fluid chamber.

The detachable aromatic nebulizing diffuser further comprises an audio source input connector mounted in an audio source connector mounting through hole on the lower housing for the connection of an external sound source for sound source input; a music control circuit board mounted on the base panel and electrically connected to the power jack and having storage means for storing voice data; and a speaker mounted on a slotted speaker mounting zone of the base panel and electrically connected to the audio source input connector and the music control circuit board for converting electrical signals from the audio source input connector and the music control circuit board into sounds.

Further, the base panel comprises a plurality of foot members located on the bottom side thereof for positioning on a flat surface to keep the air vents above the flat surface.

Further, the water baffle and the top cover can be made of a light transmissive ceramics, glass, frosted glass, plastics or acrylic, or any of a variety of transparent, translucent, partially transparent or partially translucent materials.

The detachable aromatic nebulizing diffuser further comprises a water lever sensor and a light source carried on the ultrasonic oscillator. The water level sensor is disposed inside the fluid chamber to detect the level of the contained aromatic fluid. The light source is controlled to emit light in illuminating the fluid chamber of the fluid container during operation of the ultrasonic oscillator.

Further the top muzzle of the top cover slopes in one direction. When the detachable aromatic nebulizing diffuser is positioned in a corner area in a house, the top muzzle of the top cover guides the generated fine mist toward the open space in the house.

DETAILED DESCRIPTION OF THE PREFERRED EMBODIMENT

Figure 1:
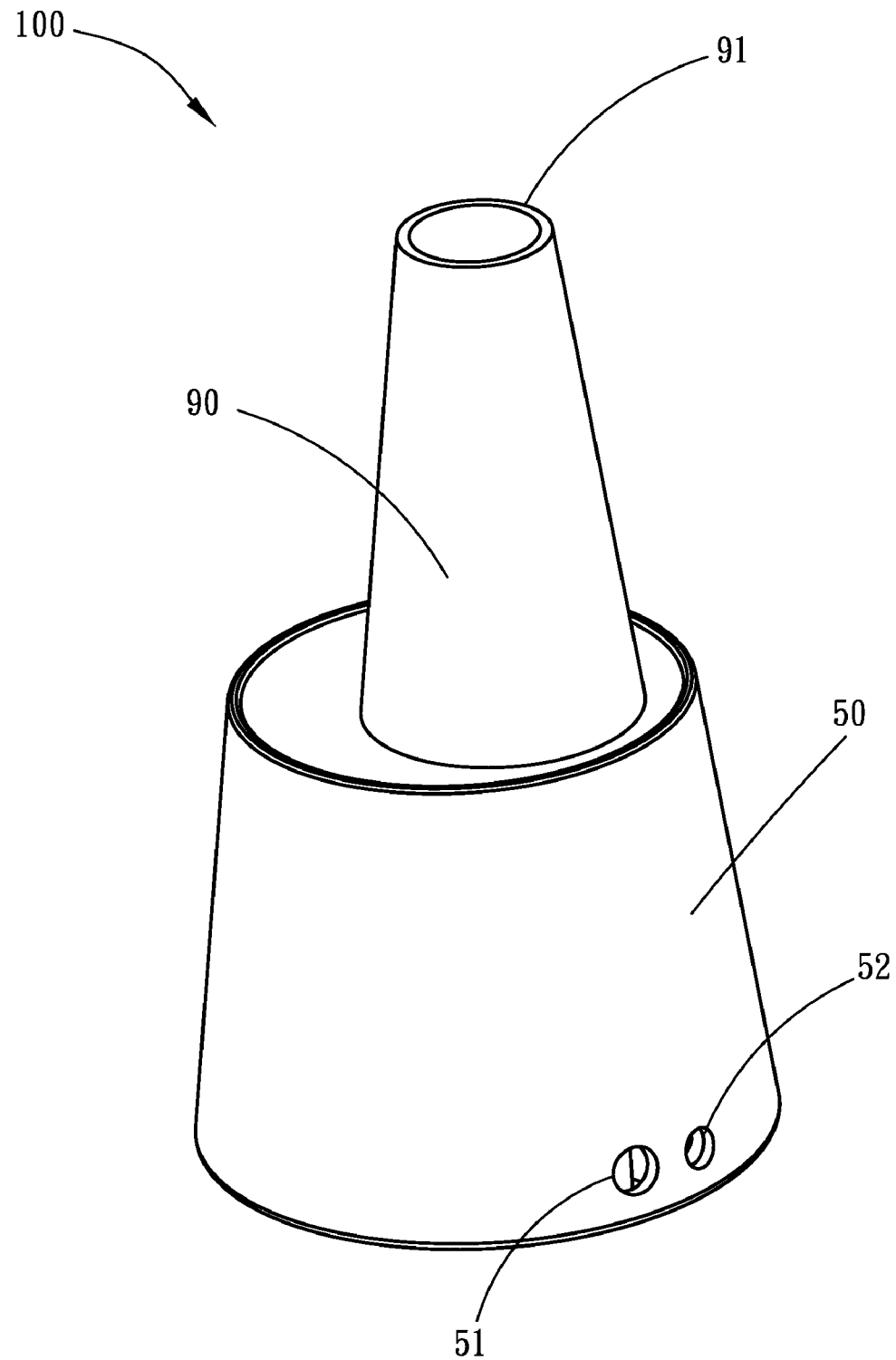
FIG. 1 is an elevational view of a detachable aromatic nebulizing diffuser in accordance with the present invention.
Figure 5:
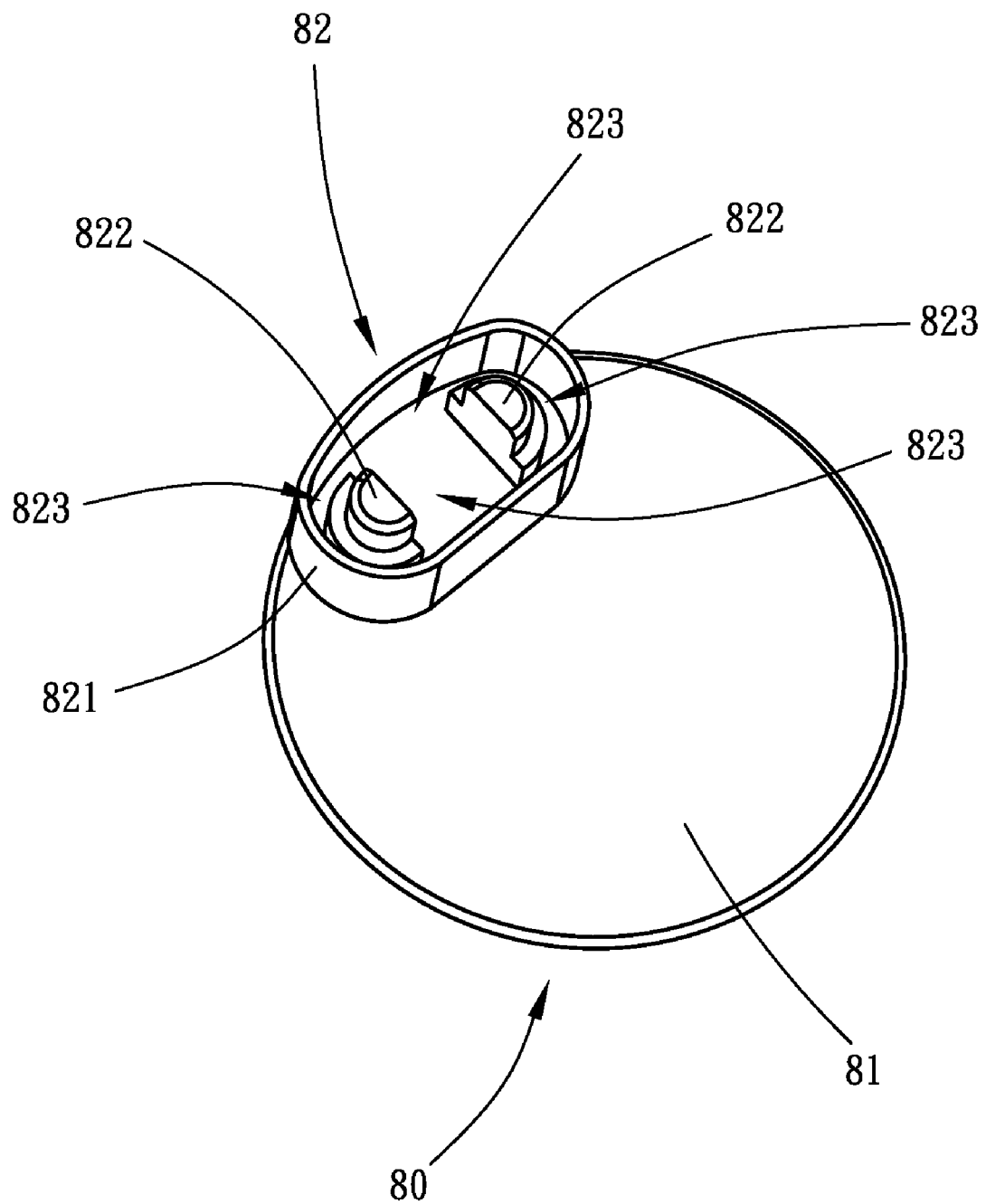
FIG. 5 is an oblique bottom view of a part of the detachable aromatic nebulizing diffuser in accordance with the present invention, showing the structure of the water baffle.

Referring to FIGS. 1 and 5, a detachable aromatic nebulizing diffuser 100 in accordance with a first embodiment of the present invention is shown comprising a base panel 10, a power jack 21, an electric fan 40, a lower housing 50, a fluid container 60, a ultrasonic oscillator 70, a water baffle 80 and a top cover 90.

Figure 2:
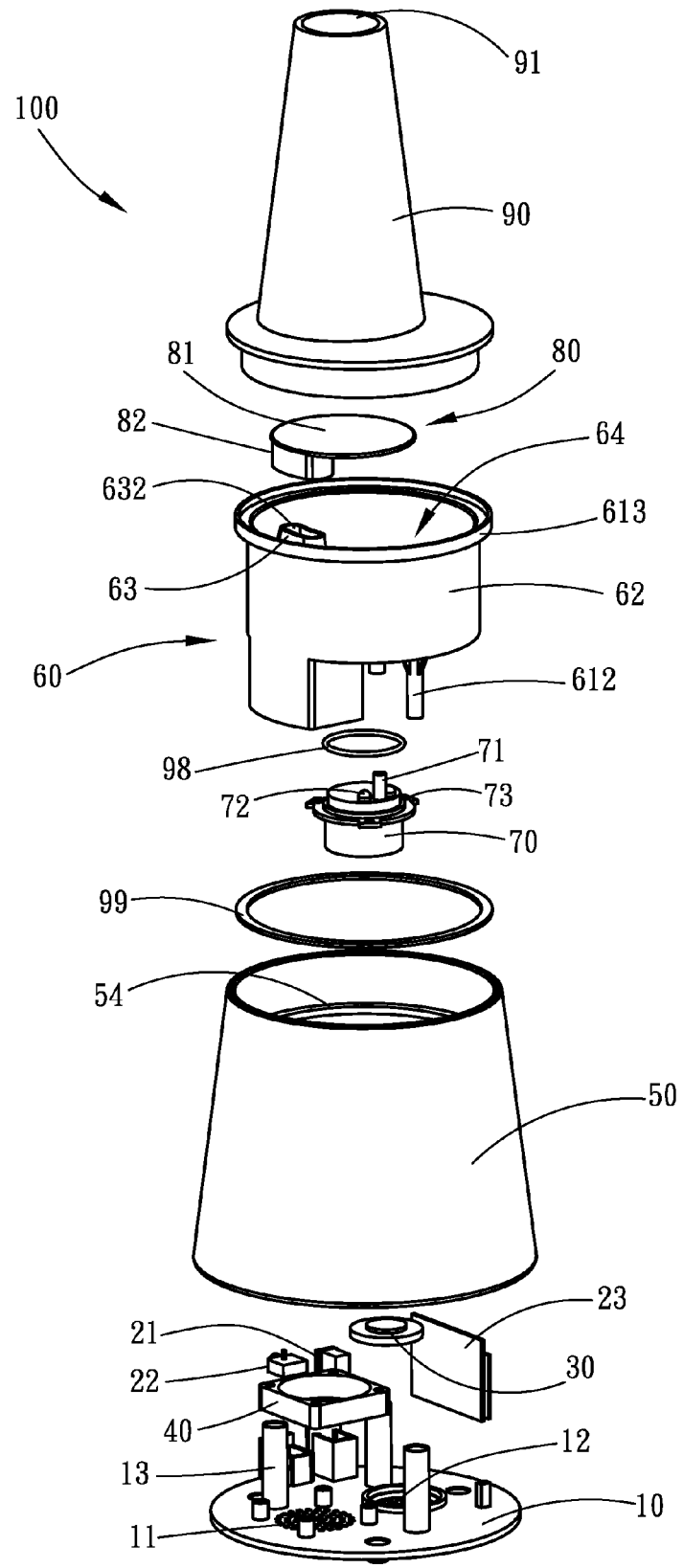
FIG. 2 is an exploded view of the detachable aromatic nebulizing diffuser in accordance with the present invention.
Figure 3:
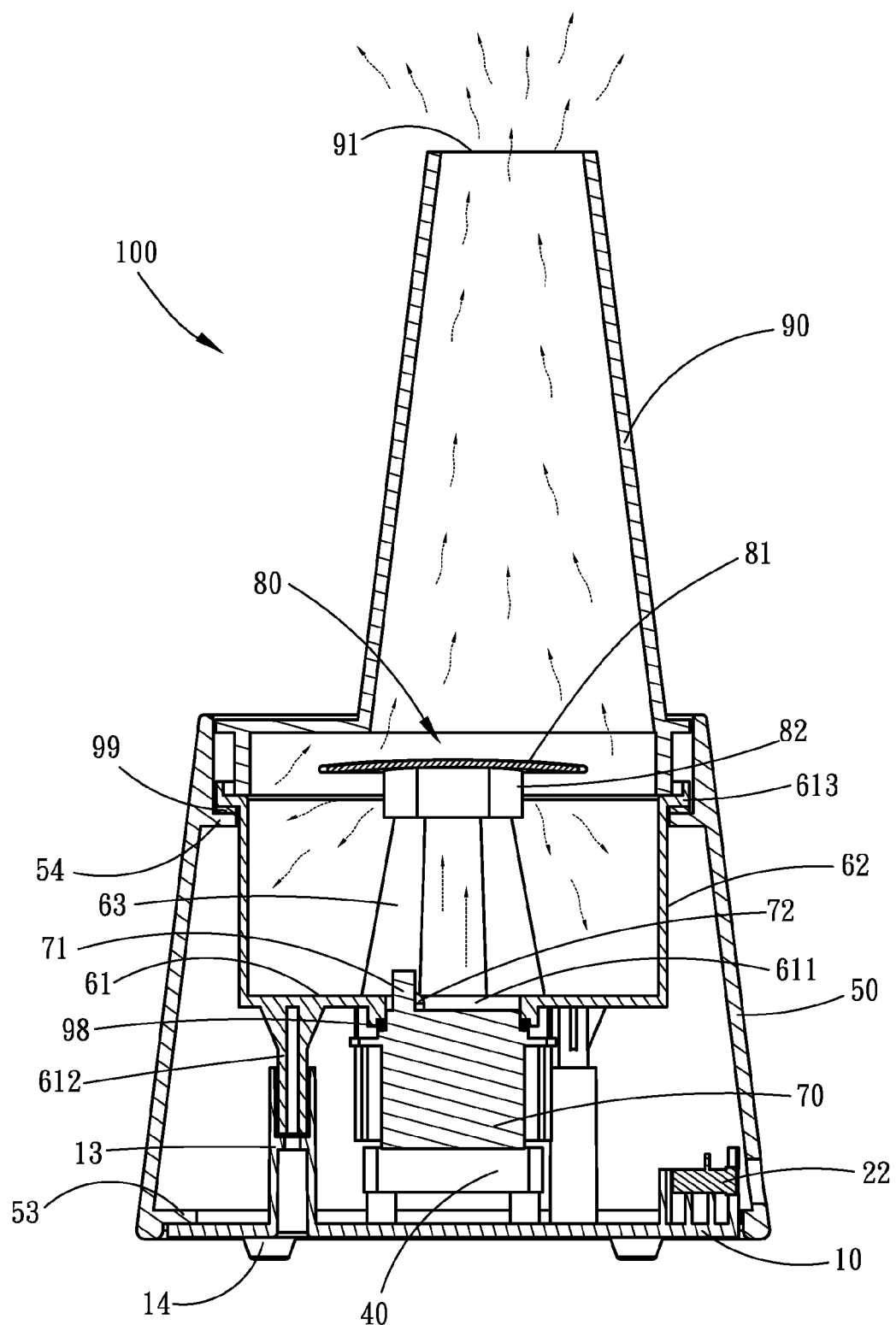
FIG. 3 is a sectional side view of the detachable aromatic nebulizing diffuser in accordance with the present invention.
Figure 4:
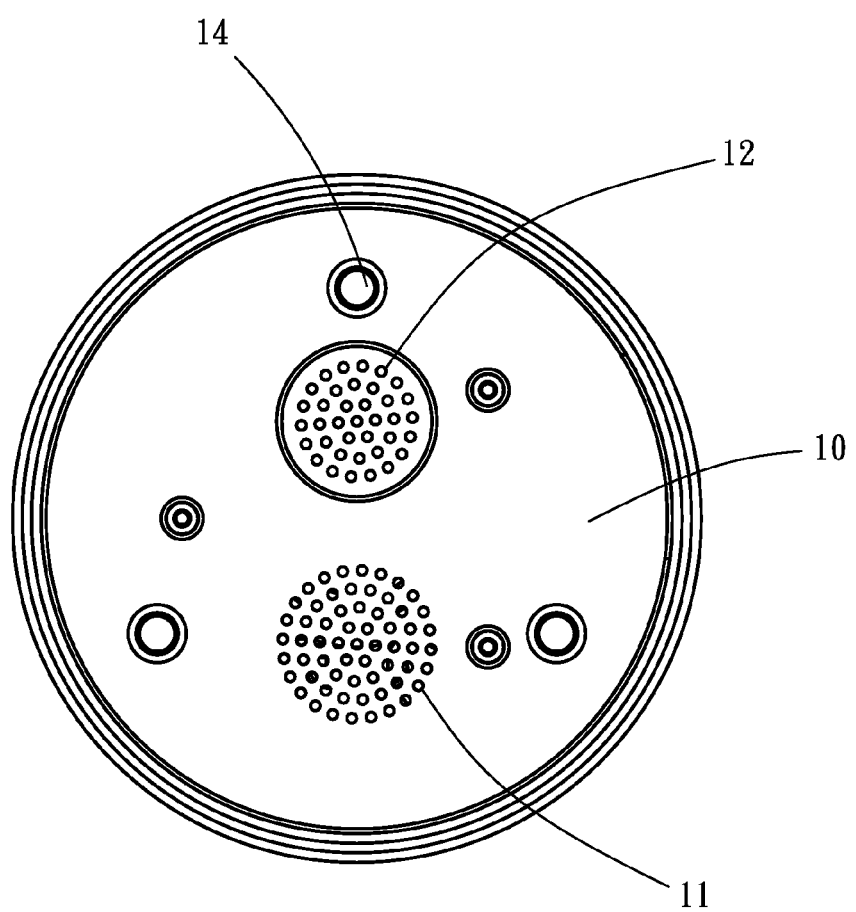
FIG. 4 is a bottom view of the detachable aromatic nebulizing diffuser in accordance with the present invention.

Referring to FIGS. 2~4, the base panel 10 has a plurality of air vents 11 cut through the top and bottom walls thereof and a plurality of tubular upright posts 13 perpendicularly extended from the top wall.

Referring to FIG. 2, the power jack 21 is mounted on the base panel 10 for the connection of an external power cable for power input.

Referring to FIG. 2, the electric fan 40 is mounted on the base panel 10 corresponding to the air vents 11 and electrically connected to the power jack 21 to obtain the necessary working voltage from the power jack 21 for drawing outside fresh air into the inside of the detachable nebulizing diffuser 100.

Referring to FIGS. 1~4, the lower housing 50 is a hollow cylindrical shell surrounding the base panel 10, the electric fan 40 and the fluid container 60.

Figure 7:
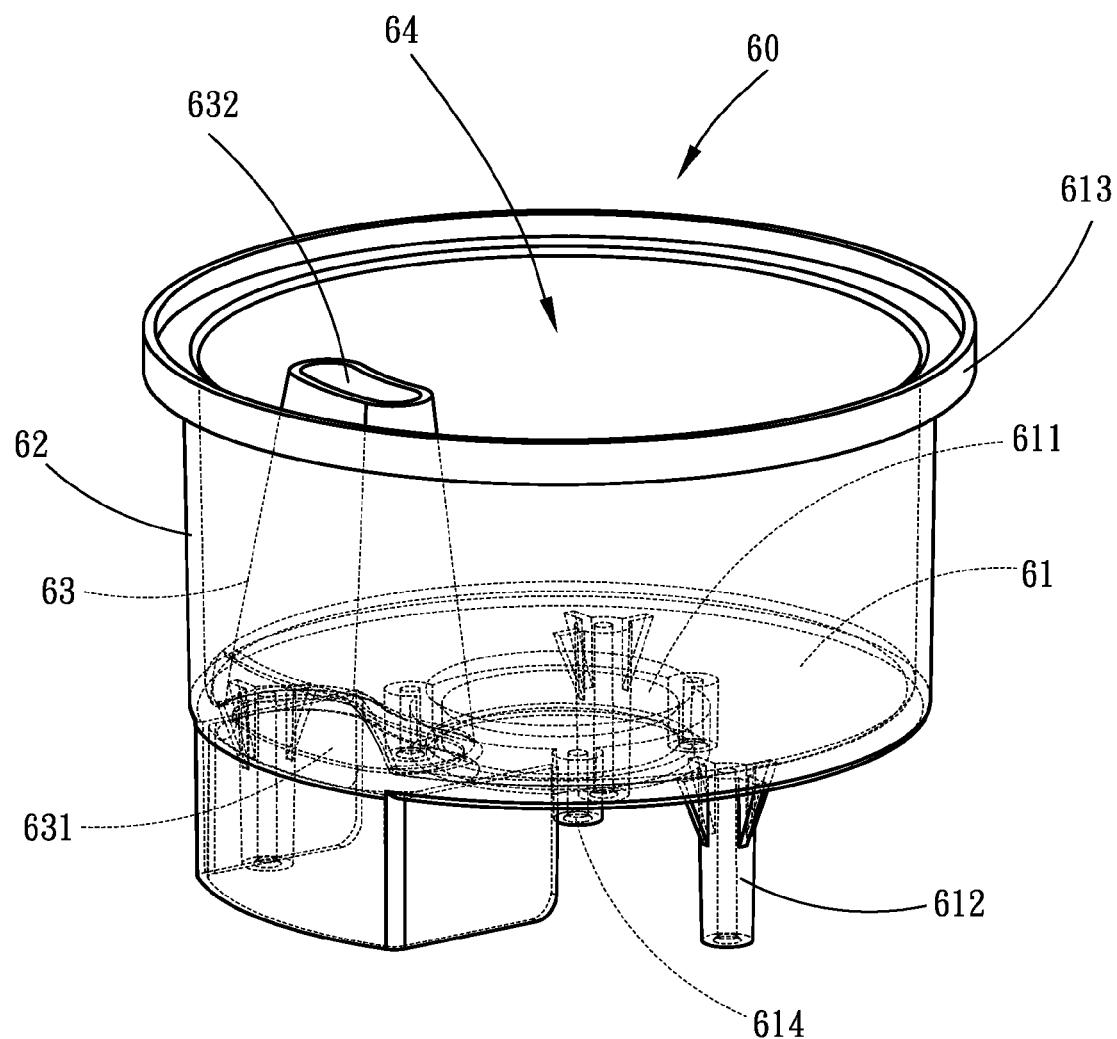
FIG. 7 is a perspective view of a part of the detachable aromatic nebulizing diffuser in accordance with the present invention, showing the structure of the fluid container.

Referring to FIGS. 2, 3 and 7, the fluid container 60 comprises a horizontal bottom wall 61, a vertical peripheral wall 62 upwardly extended from the border of the horizontal bottom wall 61, a fluid chamber 63 surrounded by the horizontal bottom wall 61 and the vertical peripheral wall 62, an air duct 63 suspending in the fluid chamber 64, a mounting hole 611 cut through the horizontal bottom wall 61 at the center and a plurality of bottom mounting rods 612 perpendicularly downwardly extended from the horizontal bottom wall 61 and respectively detachably plugged into the tubular upright posts 13 of the base panel 10. The air duct 63 has an air inlet 631 disposed at the bottom side thereof and inserted into the horizontal bottom wall 61 and facing the electric fan 20 for guiding in currents of air from the electric fan 40, an air outlet 632 disposed at the top side thereof, and a diameter gradually reducing in direction from the air inlet 631 toward the air outlet 632. The fluid container 60 is mounted in the lower housing 50 with the bottom mounting rods 612 respectively detachably plugged into the tubular upright posts 13 of the base panel 10. Thus, the fluid container 60, the base panel 10 and the lower housing 50 are fastened together, keeping the air inlet 631 in vertical alignment with the electric fan 40. Further, the bottom mounting rods 612 can be made having an inner thread so that screws (not shown) can be driven through the base panel 10 into the bottom mounting rods 612 of the fluid container 60 to affix the respective bottom mounting rods 612 of the fluid container 60 to the respective tubular upright posts 13 of the bottom panel 10.

The aforesaid lower housing 50 and fluid container 60 can be made of ceramics, facilitating cleaning and preventing corrosion of essential oils or aromatic fluids.

Referring to FIGS. 2 and 3, the ultrasonic oscillator 70 is mounted in the mounting hole 611 of the horizontal bottom wall 61 of the fluid container 60 and electrically connected to the power jack 21 to obtain the necessary working voltage from the power jack 21.

Referring to FIGS. 2, 3 and 5, the water baffle 80 comprises a tongue plate 81 and a pipe connector 82 connected to the tongue plate 81. The pipe connector 82 comprises a connector housing 821 and two retaining rods 822 suspending in the connector housing 821. The two retaining rods 822 are plugged into the air outlet 632 of the air duct 63 to hold the tongue plate 81 above the ultrasonic oscillator 70 and the aromatic fluid in the fluid chamber 64. The two retaining rods 822 and the connector housing 821 define at least one air jet 823 for reversing the flowing direction of the flow of air from the air outlet 632 of the air duct 63 toward the aromatic fluid in the fluid chamber 64.

Referring to FIGS. 1~3, the top cover 90 is shaped like a tapered barrel having a bottom opening 92 at the bottom side and a top muzzle 91 at the top side opposite to the bottom opening 92. By means of the bottom opening 92, the bottom side of the top cover 90 is vertically coupled to the fluid container 60, keeping the top muzzle 91 in communication with the fluid chamber 64.

After understanding of the structural details of the component parts of the detachable aromatic nebulizing diffuser 100 and their arrangement, the operation of the detachable aromatic nebulizing diffuser 100 is described hereinafter.

At first, an aromatic fluid (for example: essential oil and water mixture) is filled in the fluid chamber 64 of the fluid container 60, and then the ultrasonic oscillator 70 is turned on to oscillate, oscillating the aromatic fluid into a fine mist of aromatic fluid droplets. At the same time, the electric fan 40 is started to draw outside fresh air into the lower housing 50 through the air vents 11 on the base panel 10. The intake currents of air are guided through the air inlet 631 and air outlet 632 of the air duct 63 into the fluid chamber 64 via the at least one air jet 823 of the pipe connector 82 to further carry the generated fine mist of aromatic fluid droplets through the bottom opening 92 and top muzzle 91 of the top cover 90 into the outside open air.

Because the diameter of the air duct 63 reduces gradually in direction from the air inlet 631 toward the air outlet 632, the air pressure of the intake flow of air increases gradually when it is flowing through the air duct 63 into the pipe connector 82 of the water baffle 80. When the intake flow of air flows into the pipe connector 82, it is stopped by the connector housing 821 and forced to flow out of at least one air jet 823 toward the aromatic fluid in the fluid chamber 64, so that an uplifting flow of air is produced to carry the generated fine mist of aromatic fluid molecules through the top muzzle 91 of the top cover 90 to the outside open air rapidly, avoiding impact of aromatic fluid molecules and condensation of the fine mist of aromatic fluid molecules into fluid in the top cover 90. Therefore, an uplifting, therapeutic, aromatic environment is instantly created in your home or office. Further, the bottom side of the top cover 90 is detachably coupled to the top side of the fluid container 60. The user can directly remove the top cover 90 from the fluid container 60 and then clean the air duct 63 and the fluid chamber 64.

Referring to FIGS. 3 and 4, the base panel 10 further has a plurality of foot members 14 located on the bottom side. When the detachable aromatic nebulizing diffuser 100 is placed on a flat surface, the foot members 14 keep the air vents 11 of the base panel 10 above the flat surface at a distance, facilitating ventilation and enabling the electric fan 40 to draw sufficient currents of air into the air duct 63 for creating a fine mist of aromatic fluid molecules.

Referring to FIGS. 1, 2 and 3, the lower housing 50 comprises an inside bottom flange 53 protruded from the inside wall near the bottom side and abutted against the border area of the top wall of the base panel 10, an annular inside step 54 protruded from the inside wall near the top side, a power jack mounting through hole 51 and an audio source connector mounting through hole 52 cut through the periphery near the bottom side. The aforesaid power jack 21 is mounted in the power jack mounting through hole 51 for the connection of an external power source.

Referring to FIGS. 2 and 3, the fluid container 60 has an annular top flange 613 radially extended from the topmost edge of the vertical peripheral wall 62 and supported on the annular inside step 54 in the accommodation chamber 51 of the lower housing 50. Further, a rubber water seal 99 is set in between the annular top flange 613 of the fluid container 60 and the annular inside step 54 of the lower housing 50 to seal the gap.

Referring to FIGS. 2 and 3, the ultrasonic oscillator 70 has a control circuit built therein that oscillates ultrasonic waves having a frequency higher than several million cycles per second. The ultrasonic oscillator 70 is mounted in the mounting hole 611 of the horizontal bottom wall 61 of the fluid container 60 and sealed with a rubber water seal 98.

Referring to FIGS. 2, 3 and 7, the ultrasonic oscillator 70 has a plurality of mounting through holes 73 spaced around the border area thereof; the fluid container 60 has a plurality of mounting through holes 614 located on the horizontal bottom wall 61 and respectively affixed to the mounting through holes 73 of the ultrasonic oscillator 70 by screws (not shown).

Referring to FIGS. 2 and 3, the ultrasonic oscillator 70 carries a water lever sensor 71 and a light source 72. The water level sensor 71 is disposed in the fluid chamber 64 to detect the level of the contained aromatic fluid. The light source 72 is controllable to emit light, thereby illuminating the fluid chamber 64 and the top cover 90. The internal control circuit of the ultrasonic oscillator 70 controls the operation of the ultrasonic oscillator 70, the water lever sensor 71 and a light source 72. When the level of the aromatic fluid in the fluid chamber 64 is below a predetermined value, the control circuit of the ultrasonic oscillator 70 cuts off power supply from the ultrasonic oscillator 70, preventing damage. Further, the light source 72 can be comprised of at least one red LED component, at least one blue LED component, and/or at least one green LED component, or at least one multi-color LED component that emits red, blue and green light. Subject to the control of the internal control circuit of the ultrasonic oscillator 70, the light source 72 emits light of mixed color onto the periphery of the top cover 90 and/or the fluid container 60 and/or the water baffle 80, producing colorful lighting effects. Further, the top cover 90, the fluid container 60 and/or the water baffle 80 can be made of any of light transmissive ceramics, glass, frosted glass, plastics, acrylic, or any of a variety of transparent or translucent materials that allow light to pass through.

Because the component parts of the aromatic nebulizing diffuser can be conveniently and detachably assembled, the invention facilitates cleaning of the aromatic nebulizing diffuser.

Referring to FIGS. 1~3, the detachable aromatic nebulizing diffuser 100 further comprises an audio source input connector 22 mounted in the audio source connector mounting through hole 52 of the lower housing 50 for the connection of an external sound source, for example, a music player or multimedia storage device (not shown) for sound source input.

Referring to FIG. 2, the detachable aromatic nebulizing diffuser 100 further comprises a music control circuit board 23 mounted on the base panel 10 and electrically connected to the power jack 21, having means for storing natural voices, music files, animal sounds.

Referring to FIG. 2, the detachable aromatic nebulizing diffuser 100 further comprises a speaker 30 mounted on a slotted speaker mounting zone 12 of the base panel 10 and electrically connected to the audio source input connector 22 and the music control circuit board 23 to convert an electrical signal from the audio source input connector 22 or the music control circuit board 23 into sound that is driven out of the detachable aromatic nebulizing diffuser 100 through the open spaces in the slotted speaker mounting zone 12 of the base panel 10. Therefore, sound and lighting effects are created during operation of the detachable aromatic nebulizing diffuser 100. Further, the lower housing 50 shields the speaker 30, the electric fan 40 and the music control circuit board 23, enabling the audio source input connector 22 that is mounted in the audio source connector mounting through hole 52 of the lower housing 50 to communicate with external sound source means.

Figure 6:
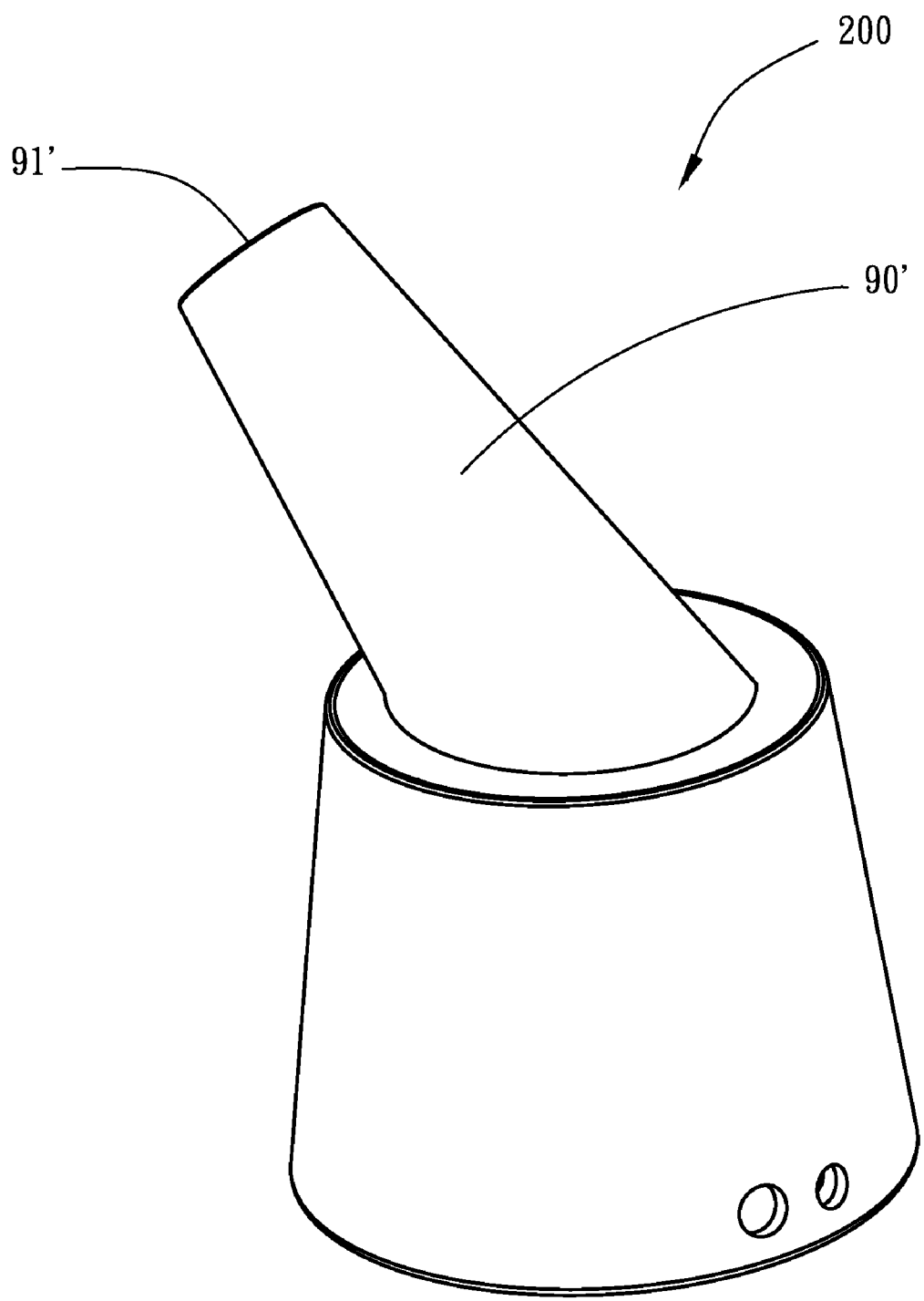
FIG. 6 is an elevational view of an alternate form of the detachable aromatic nebulizing diffuser in accordance with the present invention.

FIG. 6 illustrates an alternate form of the present invention. The detachable aromatic nebulizing diffuser, referenced by 200, of this second embodiment is substantially similar to the aforesaid first embodiment with the exception that the top cover 90' is coupled to the fluid container 60 and held in an oblique position so that the top muzzle 91' of the top cover 90' is kept tilted. The detachable aromatic nebulizing diffuser 200 can be placed in a corner area inside a house, and the top cover 90' can be rotated relative to the fluid container 60 to adjust the top muzzle 91' to the desired angular position.

Although particular embodiments of the invention have been described in detail for purposes of illustration, various modifications and enhancements may be made without What the invention claimed is:

1. A detachable aromatic nebulizing diffuser, comprising:
a base panel, said base panel comprising a plurality of air vents cut through top and bottom walls thereof and a plurality of tubular upright posts perpendicularly upwardly extended from the top wall;
an electric fan mounted on said base panel corresponding to said air vents and operable to draw outside fresh air upwardly through said air vents;
a fluid container, said fluid container comprising a horizontal bottom wall, a vertical peripheral wall, a fluid chamber surrounded by the horizontal bottom wall and the vertical peripheral wall and holding an aromatic fluid, an air duct suspending in said fluid chamber, said air duct having an air inlet disposed at a bottom side of said horizontal bottom wall and facing the electric fan for guiding in currents of air from the electric fan, an air outlet disposed at a top side thereof, and a diameter gradually reducing in direction from said air inlet toward said air outlet, a plurality of bottom mounting rods perpendicularly downwardly extended from the horizontal bottom wall and respectively detachably plugged into said tubular upright posts of said base panel, and a center mounting hole cut through said horizontal bottom wall at the center;
an ultrasonic oscillator mounted in the center mounting hole of said fluid container for generating oscillation energy to cause the aromatic fluid in said fluid chamber into a fine mist;
a power jack mounted on said base panel and electrically connected with said electric fan and said ultrasonic oscillator for providing said electric fan and said ultrasonic oscillator with the necessary working voltage;
a water baffle, said water baffle comprising a tongue plate and a pipe connector connected to the tongue plate, said pipe connector comprising a connector housing and two retaining rods suspending in said connector housing and plugged into the air outlet of the air duct to hold the tongue plate above said ultrasonic oscillator and the aromatic fluid contained in said fluid chamber, said two retaining rods and said connector housing defining at least one air jet for ejection of a flow of air from said air outlet of said air duct toward the aromatic fluid in said fluid chamber;
a lower housing surrounding said base panel, said power jack, said electric fan, said fluid container and said ultrasonic oscillator; and
a top cover covering said fluid container and said lower housing, said top cover comprising a bottom opening disposed at a bottom side thereof and coupled to said fluid container and a top muzzle disposed at a top side thereof in communication with said bottom opening and said fluid chamber.

2. The detachable aromatic nebulizing diffuser as claimed in claim 1, further comprising:
an audio source input connector mounted in an audio source connector mounting through hole on said lower housing for the connection of an external sound source for sound source input;
a music control circuit board mounted on said base panel and electrically connected to said power jack, said music control circuit board comprising storage means for storing voice data; and
a speaker mounted on a slotted speaker mounting zone of said base panel and electrically connected to said audio source input connector and said music control circuit board for converting electrical signals from said audio source input connector and said music control circuit board into sounds.

3. The detachable aromatic nebulizing diffuser as claimed in claim 1, wherein said base panel comprises a plurality of foot members located on a bottom side thereof for positioning on a flat surface to keep said air vents above the flat surface.

4. The detachable aromatic nebulizing diffuser as claimed in claim 1, wherein said lower housing comprises an inside bottom flange disposed near a bottom side thereof and abutted against the border area of said base panel, and an annular inside step disposed near a top side thereof for supporting said fluid container inside said lower housing; said fluid container comprises an annular top flange radially extended from the topmost edge of the vertical peripheral wall thereof and supported on the annular inside step of said lower housing.

5. The detachable aromatic nebulizing diffuser as claimed in claim 1, wherein said water baffle is made of a light transmissive material.

6. The detachable aromatic nebulizing diffuser as claimed in claim 1, wherein said top cover is made of a light transmissive material.

7. The detachable aromatic nebulizing diffuser as claimed in claim 4, further comprising a first rubber water seal set between the annular top flange of said fluid container and the annular inside step of said lower housing, and a second rubber water seal set between said ultrasonic oscillator and the center mounting hole of said fluid container.

8. The detachable aromatic nebulizing diffuser as claimed in claim 1, further comprising a water lever sensor and a light source carried on said ultrasonic oscillator, said water level sensor being disposed in said fluid chamber to detect the level of the contained aromatic fluid, said light source being controlled to emit light in illuminating said fluid chamber during operation of said ultrasonic oscillator.

9. The detachable aromatic nebulizing diffuser as claimed in claim 8, wherein said light source comprises at least one red LED component, at least one blue LED component, and/or at least one green LED component, or at least one multi-color LED component that emits light of mixed color.

10. The detachable aromatic nebulizing diffuser as claimed in claim 1, wherein said top muzzle of said top cover is kept in a tilted position.

* * * * *